US008801696B2

(12) United States Patent
Graffam et al.

(10) Patent No.: US 8,801,696 B2
(45) Date of Patent: Aug. 12, 2014

(54) CATHETER HUB ASSEMBLY

(75) Inventors: Richard Graffam, Marlborough, MA (US); Ben Morris, Jeffersonville, IN (US); Chuck Bourgeois, Wilmington, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 634 days.

(21) Appl. No.: 12/610,037

(22) Filed: Oct. 30, 2009

(65) Prior Publication Data

US 2011/0106059 A1   May 5, 2011

(51) Int. Cl.
*A61M 25/16* (2006.01)

(52) U.S. Cl.
USPC .......................................... 604/535; 604/540

(58) Field of Classification Search
USPC ............ 604/93.01, 95.04, 104, 528, 533, 540
See application file for complete search history.

(56) References Cited

U.S. PATENT DOCUMENTS

| | | |
|---|---|---|
| 4,740,195 A | 4/1988 | Lanciano |
| 5,419,764 A | 5/1995 | Roll |
| 5,472,435 A | 12/1995 | Sutton |
| 5,941,849 A | 8/1999 | Amos, Jr. |
| 6,042,577 A | 3/2000 | Chu |
| 6,159,177 A | 12/2000 | Amos, Jr. et al. |
| 6,231,542 B1 | 5/2001 | Amos, Jr. |
| 6,315,789 B1 | 11/2001 | Cragg |
| 6,547,761 B2 | 4/2003 | Liu |
| 6,673,060 B1 | 1/2004 | Fleming, III |
| 6,893,418 B2 | 5/2005 | Liu |
| 7,351,222 B2 | 4/2008 | Sauvageau |
| 2001/0049490 A1 | 12/2001 | Slanda et al. |
| 2005/0107739 A1 | 5/2005 | Palma |

OTHER PUBLICATIONS

International Search Report, PCT/US2010/54875, Oct. 29, 2010.

*Primary Examiner* — Melanie Hand
(74) *Attorney, Agent, or Firm* — Peter J. Flora

(57) ABSTRACT

A catheter hub assembly comprising a hub body having a proximal end, a distal end, and a shaft having a first suture hole, a collar and a snap ring; a hub knob having a second suture hole and rotatably coupled to the hub body; and a hub cap having a snap rut wherein the snap ring fits into the snap rut. In one embodiment, the hub body includes a lock element; the hub knob includes a first tab element and a second tab element; and the hub cap includes a groove; wherein the first tab element engages the lock element; and wherein the second tab element engages the groove. In another embodiment, the hub cap includes a lock element comprising a resilient tab and a catch; the hub knob includes a catch tab; wherein the catch tab engages the catch of the lock element.

11 Claims, 8 Drawing Sheets

CATHETER HUB ASSEMBLY

FIELD OF THE INVENTION

The invention generally relates to the field of catheters and more particularly to a catheter having a mechanism for retaining a distal end of the catheter in a predetermined configuration within a patient.

BACKGROUND OF THE INVENTION

Drainage catheters may be used where fluid has collected in the body and requires removal. Examples include the drainage of a hematoma (collection of blood), billoma (collection of bile), or urinoma (collection of urine). Drainage catheters may be used to percutaneously drain an abscess or pocket of fluid in the body to the exterior by means of gravity or negative pressure. Typical abscess fluids include biliary, nephrostomy, pleural, urinary, and mediastinal collection.

Catheterization can be used to drain the bladder after surgery or when the genitourinary system is plugged by an obstruction. Typically, drainage catheters may lie in a patient for a fairly long period of time. Accordingly, catheters have been developed with anchor structures to prevent inadvertent removal of the catheter from a patient. A "pigtail loop" as is disclosed in U.S. Pat. No. 6,231,542, is one such anchor and is formed by a flexible tube portion at the distal end of the catheter. The pigtail loop may be created in the catheter by forming the flexible tube of the catheter of a memory material. A stiff cannula or similar implement may be inserted through the catheter lumen to straighten the pigtail loop for introduction into the patient. The distal end of the flexible tube returns to the pigtail loop configuration after the cannula is removed. Alternatively, the end of the catheter can be flexible and pulled into the pigtail or other anchoring configuration by pulling a tension member, e.g. a suture wire that extends from the distal end of the catheter to and out of the catheter near its proximal end. The suture wire can be attached to draw ports located at two separated positions along the distal portion of the catheter. Pulling the suture juxtaposes the draw ports and forms a pigtail loop at the distal end of the catheter. A physician can secure the pigtail loop by grasping and pulling on one or more suture threads that lead distally from the pigtail loop. When the suture thread is taut, it prevents the pigtail loop from straightening by holding the juxtaposed portions of the catheter together. The catheter tip can be returned to its straight configuration by releasing the tension of the suture at its proximal end.

With some catheters, tying or locking the suture thread prevents the pigtail loop from straightening. However, if the suture thread is loosened or becomes unsecured, the pigtail loop or other anchor at the distal end of the catheter may be released and the catheter inadvertently released and withdrawn from the patient.

SUMMARY OF THE INVENTION

In accordance with one embodiment provided herein, a catheter hub assembly comprises a hub knob and a hub body disposed within the hub knob. The hub knob has an exterior surface, a through lumen and a suture hole extending from the exterior surface to the inner lumen. The hub body has a proximal end, a distal end, and a shaft having an exterior surface with an inner through lumen extending between the proximal end and the distal end. A suture hole extending from the exterior surface of the hub body to the inner lumen of the hub body. The hub knob is displaceable relative to the hub body between a first position in which the suture holes of the hub knob and hub body are aligned and a second position in which the suture holes of the hub knob and hub body are offset from one another.

In accordance with another embodiment, the catheter hub assembly includes a hub cap that is fixed to the distal end of the hub body. The hub cap may include a groove portion defining first and second stops, and the hub knob may include a limit member disposed in the hub cap groove for engaging the hub cap first and second stops when the hub knob is in the first and second positions respectively.

In accordance with another embodiment, the hub body includes a locking member that cooperates with a locking element on the hub knob to locate the hub knob in position relative to the hub body.

In accordance with a further embodiment, when the hub knob is in a first position relative to the hub body such that the suture holes of the hub body and hub knob are aligned, the limit member of the hub knob engages the first stop of the hub cap to limit displacement of the hub knob relative to the hub body in one direction. And when the hub knob is displaced in the opposite direction to the second position in which the suture holes of the hub knob and hub body are offset, the limit member engages the second stop of the hub cap to limit further displacement of the hub knob relative to the hub body in one direction and the locking member of the hub knob engages the stop of the locking element of the hub body to inhibit displacement of the hub knob relative to the hub body in the opposite direction.

In accordance with another embodiment, the catheter hub assembly includes a hub cap that is fixed to the distal end of the hub body. The hub knob may include a groove portion defining first and second stops, and the hub body may include a limit member disposed in the hub knob groove for engaging the hub knob first and second stops when the hub knob is in the first and second positions respectively.

In accordance with another embodiment, the hub knob includes a locking member that cooperates with a locking catch on the hub cap to locate the hub knob in position relative to the hub body.

In accordance with a further embodiment, when the hub knob is in a first position relative to the hub body such that the suture holes of the hub body and hub knob are aligned, the limit member of the hub body engages the first stop of the hub knob to limit displacement of the hub knob relative to the hub body in one direction. And when the hub knob is displaced in the opposite direction to the second position in which the suture holes of the hub knob and hub body are offset, the limit member engages the second stop of the hub knob to limit further displacement of the hub knob relative to the hub body in one direction and the locking member of the hub knob engages the locking catch of the hub cap to inhibit displacement of the hub knob relative to the hub body in the opposite direction.

Other systems, methods, features and advantages of the example embodiments will be or will become apparent to one with skill in the art upon examination of the following figures and detailed description.

BRIEF DESCRIPTION OF THE DRAWINGS

The details of the example embodiments, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illus

It should be noted that elements of similar structures or functions are generally represented by like reference numerals for illustrative purpose throughout the figures. It should also be noted that the figures are only intended to facilitate the description of the preferred embodiments.

DETAILED DESCRIPTION

Figure 1:
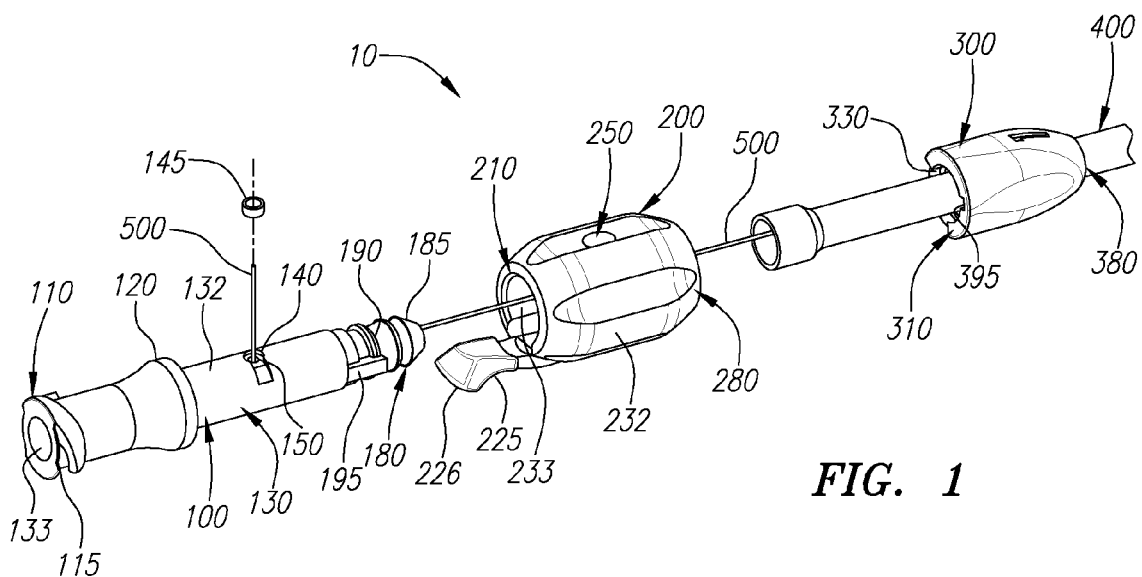
- FIG. 1 is an exploded view of the catheter hub and catheter assembly in accordance with one embodiment.
Figure 2:
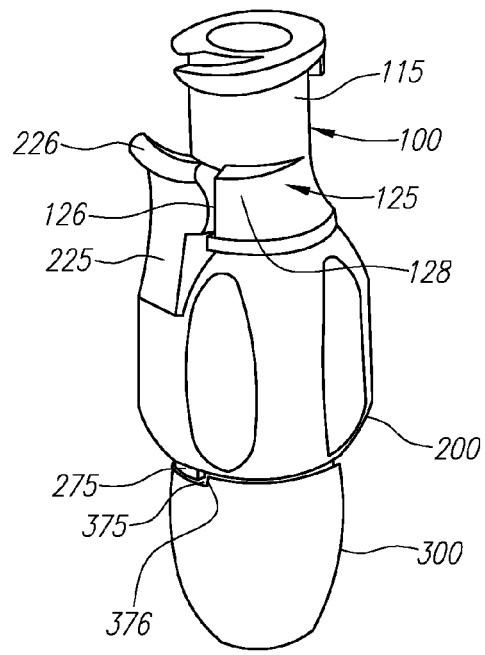
FIG. 2 is an assembled view of the catheter hub shown in FIG. 1.
Figure 3:
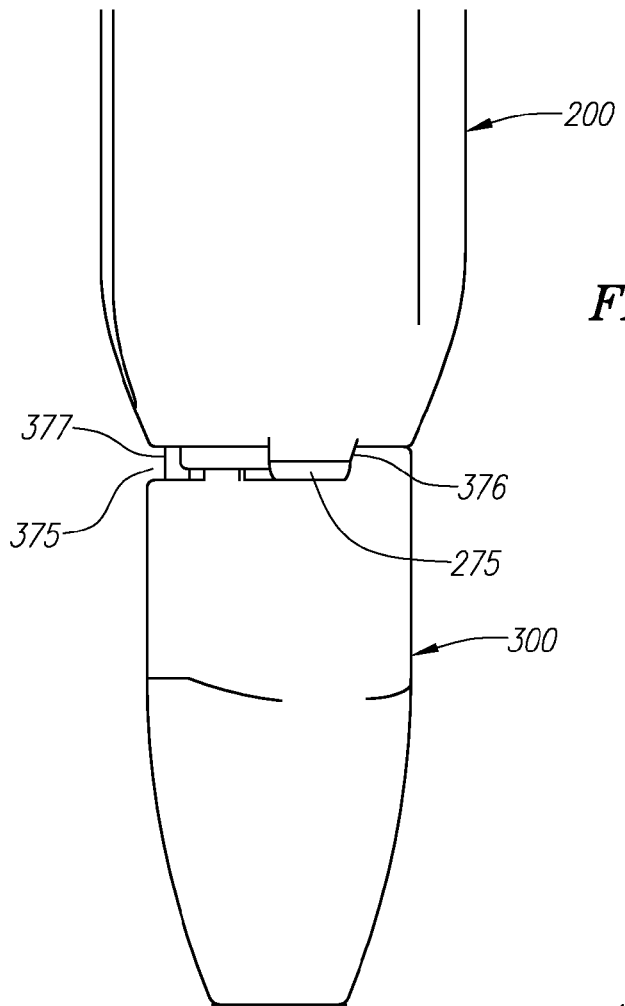
FIG. 3 is a schematic view of the hub knob and hub cap shown in FIG. 1 assembled together.
Figure 4:
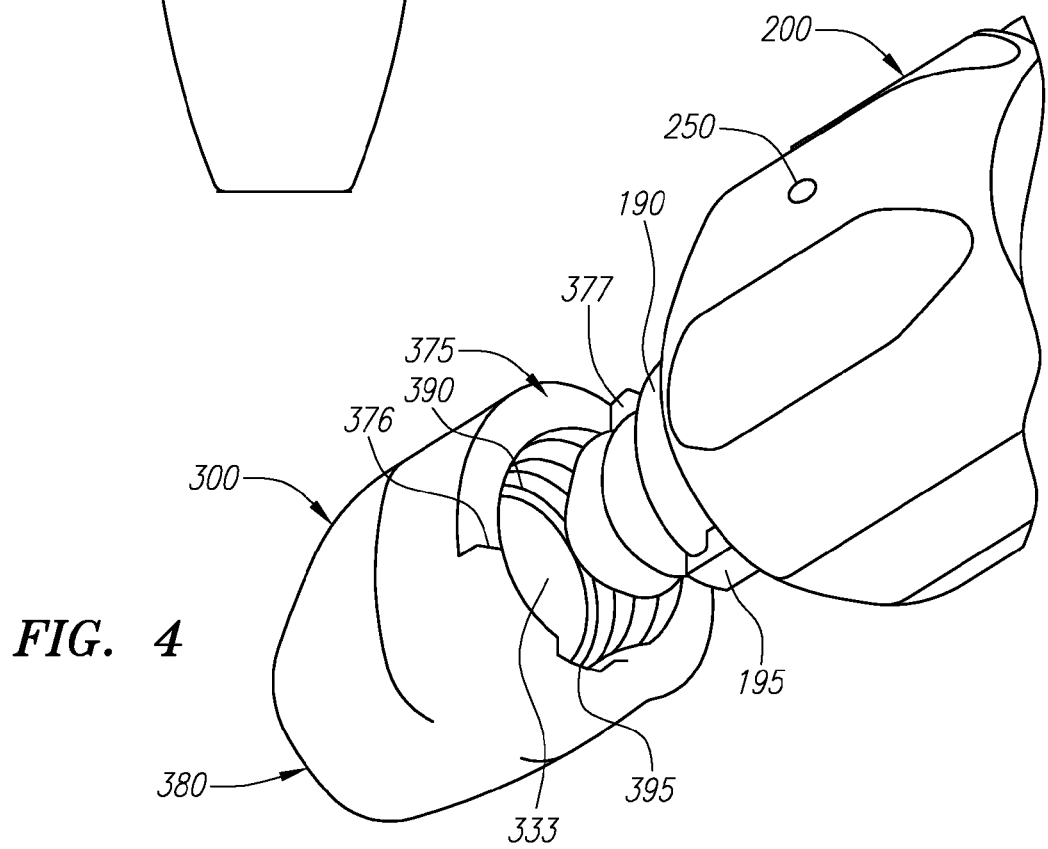
FIG. 4 is a detailed partial exploded view of the hub body, hub knob and hub cap assembly shown in FIG. 1.

Referring to FIGS. 1-2, a catheter hub assembly 10 in accordance with one embodiment includes a hub body 100, a hub knob 200, and a hub cap 300. Hub body 100 has a proximal end 110 and a distal end 180, with a shaft 130 extending between the proximal end 110 and the distal end 180. Shaft 130 has an exterior surface 132 and an inner through lumen 133. The proximal end 110 of the hub body 100 may include a Luer lock 115 for connection with other apparatuses. The hub body 100 may include a collar 120 and a lock element 125 located toward the proximal end 110 on the external surface 132 of the hub body 100. In accordance with one aspect of the invention, locking element 125 may comprise a ramp portion 128 that increases in height along the exterior surface of the hub body 100 to a stop portion 126.

The shaft 130 of the hub body 100 may include a recessed area 140 for receiving an O-ring 145. A suture hole 150 is disposed in the recessed area 140 and passes through to the inner lumen to allow one or more suture wires 500 or tension members to pass through. The O-ring 145 seals the suture hole 150 to ensure that the catheter hub 10 does not leak.

The hub body 100 may further include a flair element 185, a snap ring 190, and an alignment key 195 located adjacent the distal end 180 of the hub body 100. The flair element 185 of the hub body 100 is adapted to mate with a catheter 400.

Still referring to FIGS. 1-2, the hub knob 200 has a proximal end 210, a distal end 280, an exterior surface 232 and an inner through lumen 233 into which is received the shaft 130 of hub body 100 such that hub knob 200 is displaceable, e.g. rotatable relative to hub body 100. Preferably, collar 120 fits over the peripheral edge of proximal end 210 of hub knob 200. Hub knob 200 may also include a locking member 225 and a suture hole 250 extending from the exterior surface 232 to the inner lumen 233. Preferably locking member 225 is a resilient member that extends from the proximal end of hub knob 200 and is spring biased toward the exterior surface of hub shaft 130. It is also preferable that locking member 225 includes an outwardly flared tip portion 226 that facilitates displacing the locking member 225 in a direction away from hub body 100. Hub knob 200 may also include a limit member 275 disposed at its distal end 280.

Referring to FIGS. 1-4, the hub cap 300 has a proximal end 310, a distal end 380 and a through lumen 333. A groove 375 defining a first stop portion 376 and a second stop portion 377 may be disposed at the proximal end 310. Limit member 275 of the hub knob 200 is received in groove 375. Hub cap 300 may also include a snap groove 390 and an alignment port 395. Snap ring 190 of the hub body 100 fits into a snap rut or groove 390 of the hub cap 300 to secure the hub body 100 to the hub cap 300. The distal end 380 of the hub cap 300 is adapted to capture the catheter 400 to be secured to the flair element 185 of the hub body 100 when the catheter hub 10 is assembled. The exterior of the hub cap 300 can be used to identify the catheter French size with which it can be used. Preferably, in accordance with one aspect of the invention, alignment key 195 of hub body 100 is received within alignment port 395 of hub cap 300 to properly align hub body 100 with the hub cap 300.

Figure 5:
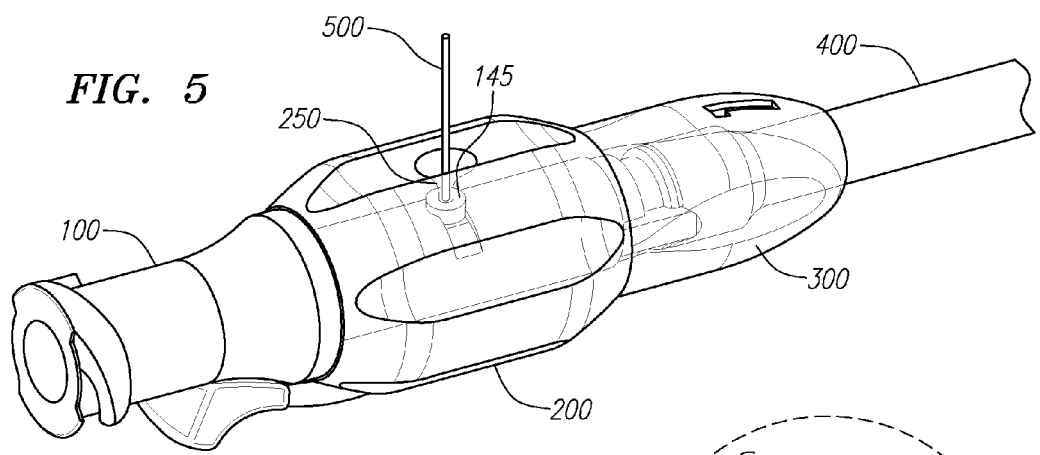
FIG. 5 is an assembled view of the catheter hub assembly shown in FIG. 1 with O-ring, suture wire, and catheter in the open position.

Referring to FIG. 5, the catheter hub 10 is shown assembled and attached to a catheter 400 with the hub knob 200 being disposed in a first open position in which the suture holes 250 and 150 are aligned with one another. Preferably, locking member 225 is disposed in a first position overlying ramp portion 128 and out of engagement with stop portion 126. It is also preferable that in this first open position, limit member 275 engages stop 376 (see FIG. 3) to prevent further rotation of hub knob in a counterclockwise direction. In this open position, suture wire 500 is freely moveable through the suture holes 250 and 150 and can be readily pulled out of hub knob 200 which effects the pulling of the flexible end 426 of catheter 400 into the pigtail configuration shown in FIG. 6. Further referring to FIG. 6 and FIG. 2, hub knob 200 may be rotated in a clockwise direction until locking member 225 traverses ramp position 128 of locking element 125 and because of its spring bias snaps into engagement with stop portion 126 of locking element 125. Stop 126 limits counter-rotation of hub knob 200 in the clockwise direction.

Figure 6:
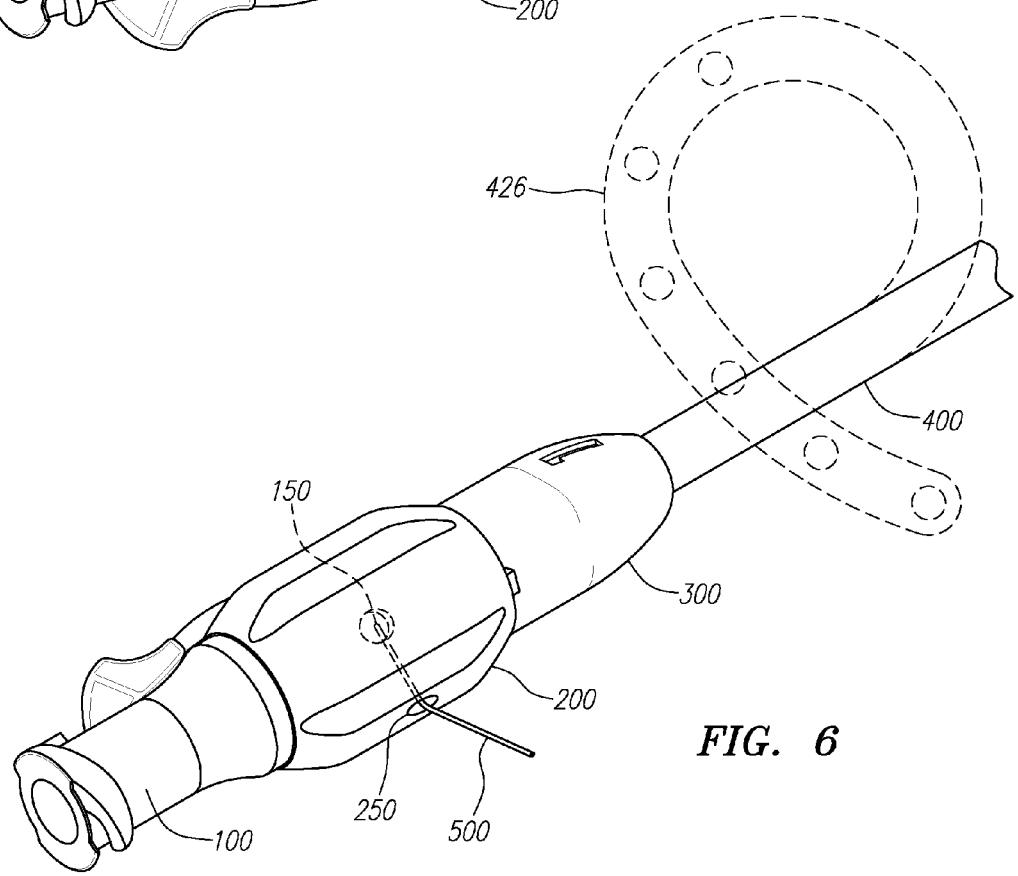
FIG. 6 is an assembled view of the catheter hub assembly shown in FIG. 1 in the closed position.

Referring to FIG. 6, this second position of hub knob 200 is a locked position because suture holes 250 and 150 are now offset relative to one another and suture wire 500 is trapped between the inside surface of hub knob 200 and the outside surface of hub body 100. This trapping or locking of suture wire 500, effectively keeps suture wire stationary so as to maintain the catheter end 426 in position, e.g., in the pigtail configuration of FIG. 6. Preferably, in this closed position, limit member 375 also engages stop 377 to prevent further rotation of hub knob 200 in a clockwise direction. To unlock the assembly, a user can pull back resilient locking member 225 to raise it over stop 126 so as to disengage it from stop 126. Hub knob 200 can then be rotated in a clockwise direction such that locking member 225 engages the ramp portion of 128 locking element 125 to the open position where suture holes 250 and 150 are again aligned and suture wire can be readily moved and the catheter pigtail configuration straightened out so that the catheter can be removed from the patient.

Figure 7:
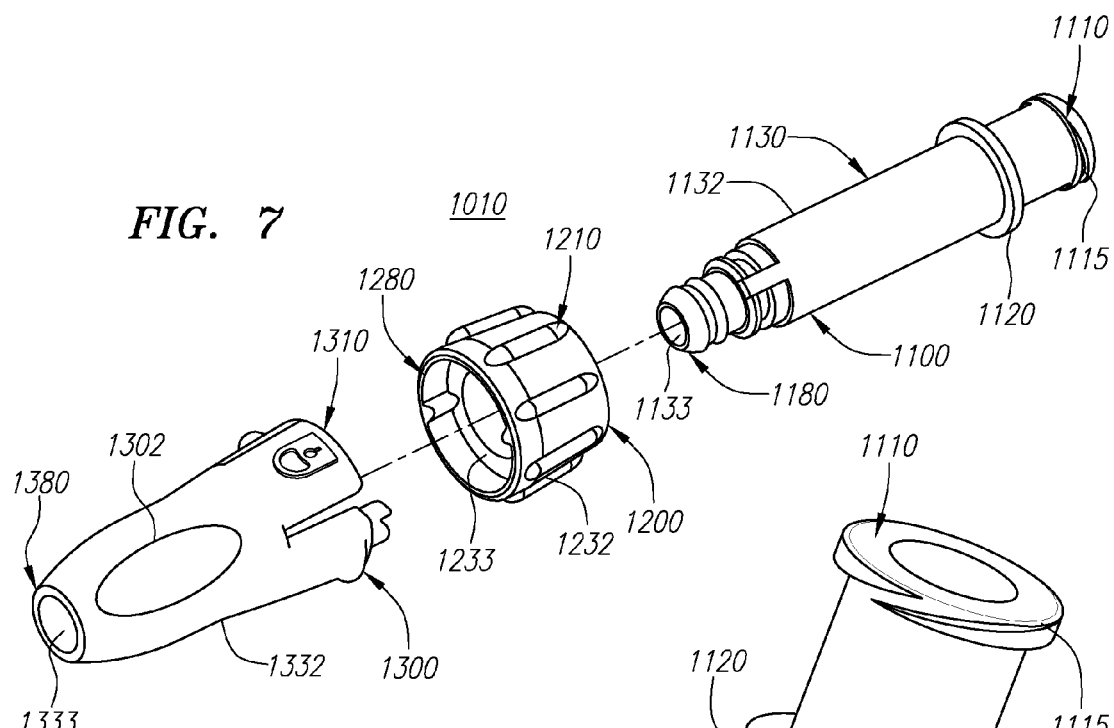
FIG. 7 is an exploded view of the catheter hub assembly in accordance with another embodiment.
Figure 8:
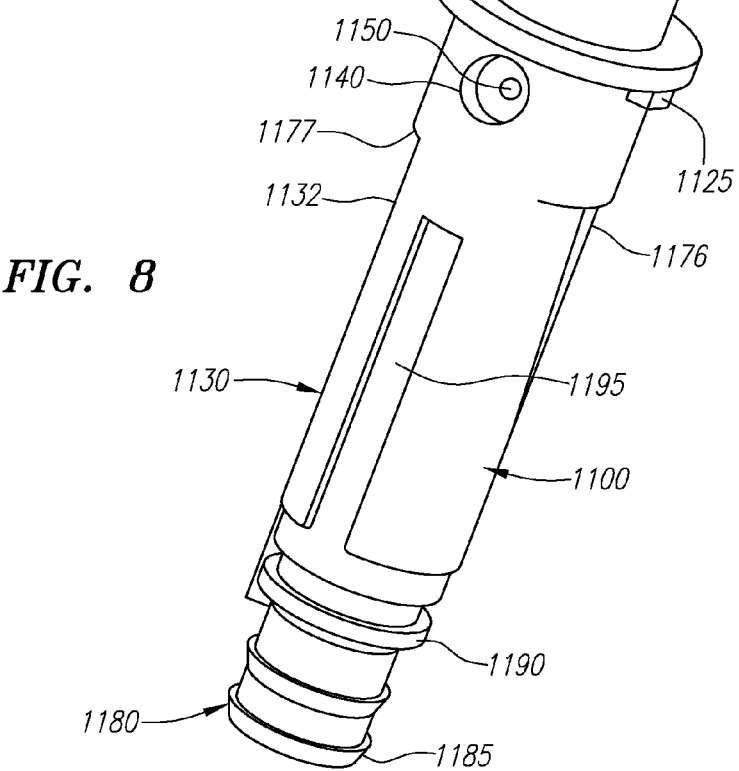
FIG. 8 is a schematic of the hub body shown in FIG. 7.
Figure 9:
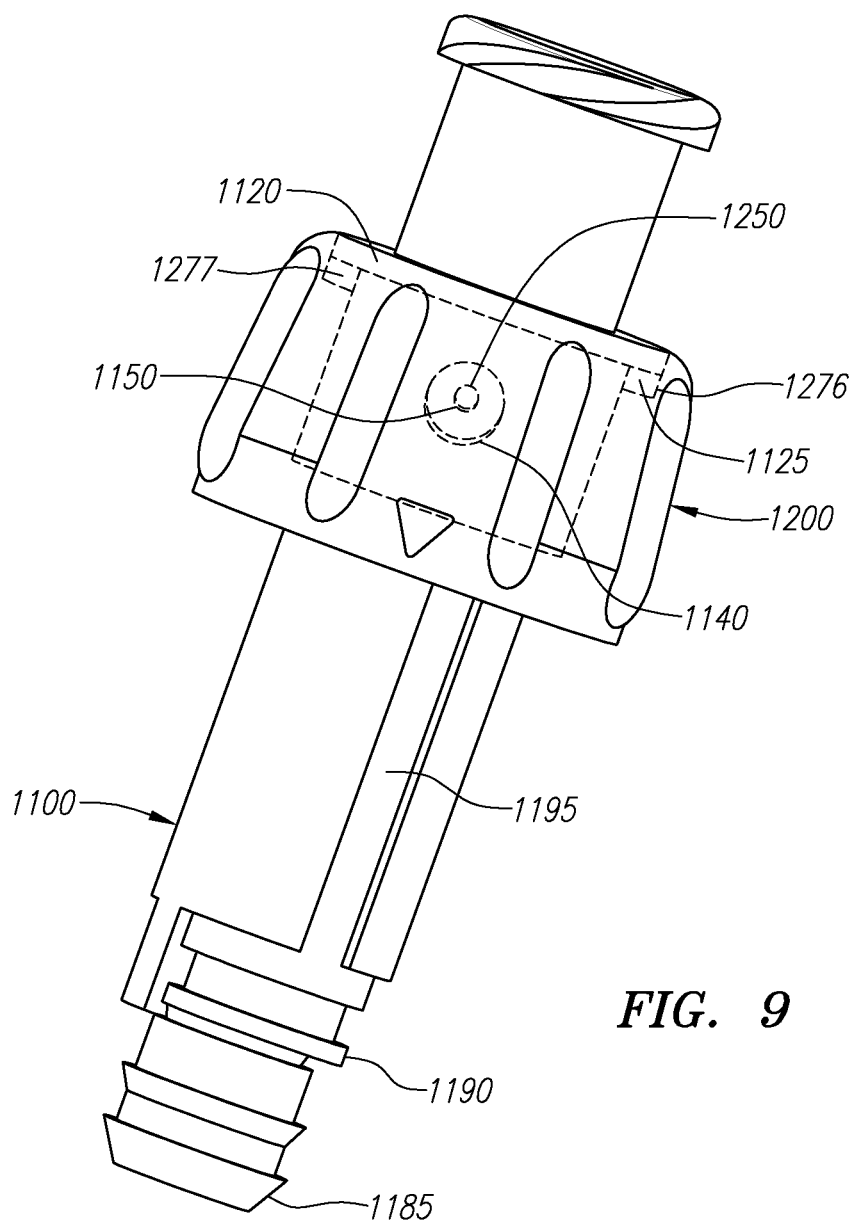
FIG. 9 is a schematic view of the hub knob and hub body shown in FIG. 7 assembled together.
Figure 10:
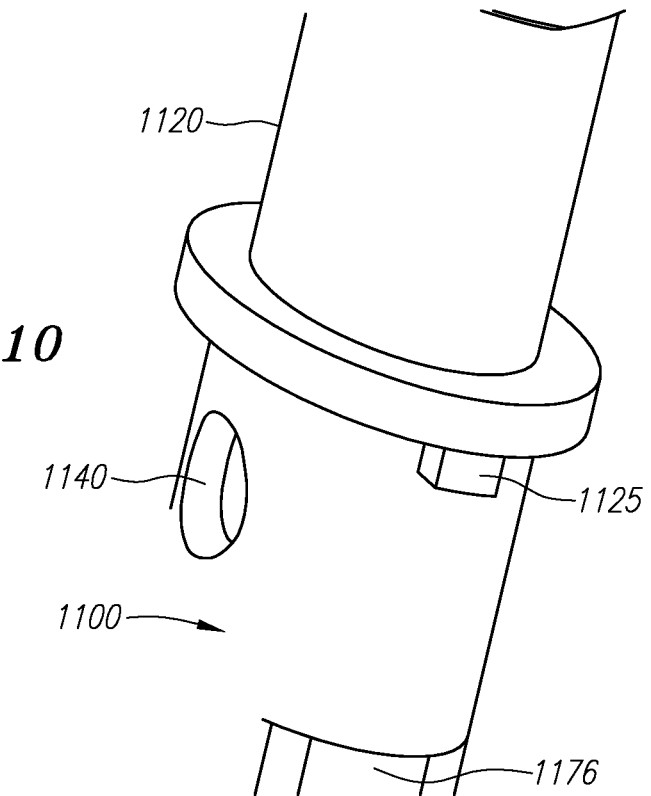
FIG. 10 is a partial schematic view of the hub body shown in FIG. 7.
Figure 11:
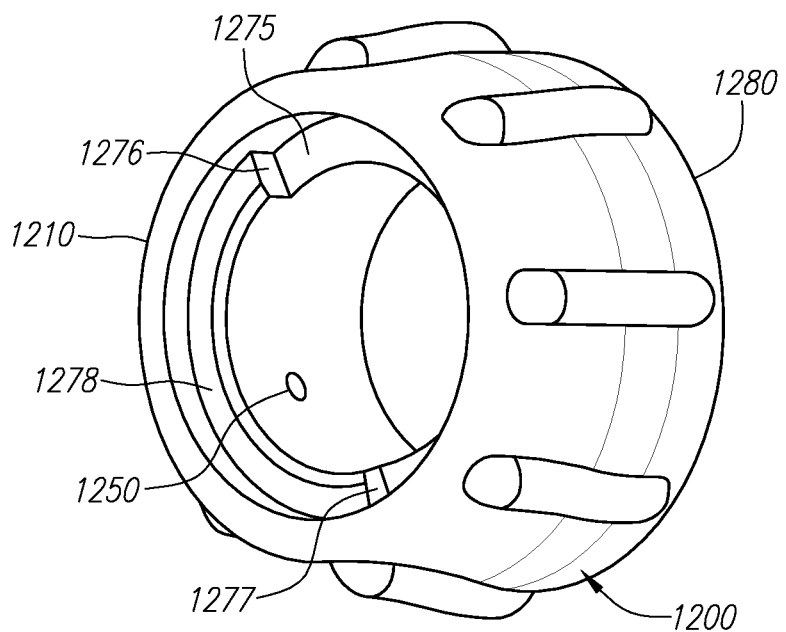
FIG. 11 is a schematic view of the proximal end of the hub knob shown in FIG. 7.
Figure 12:
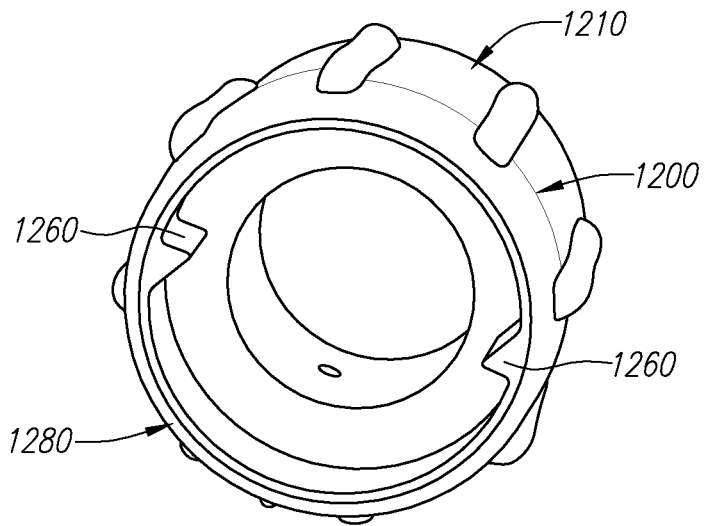
FIG. 12 is a schematic view of the distal end of the hub knob shown in FIG. 7.
Figure 13:
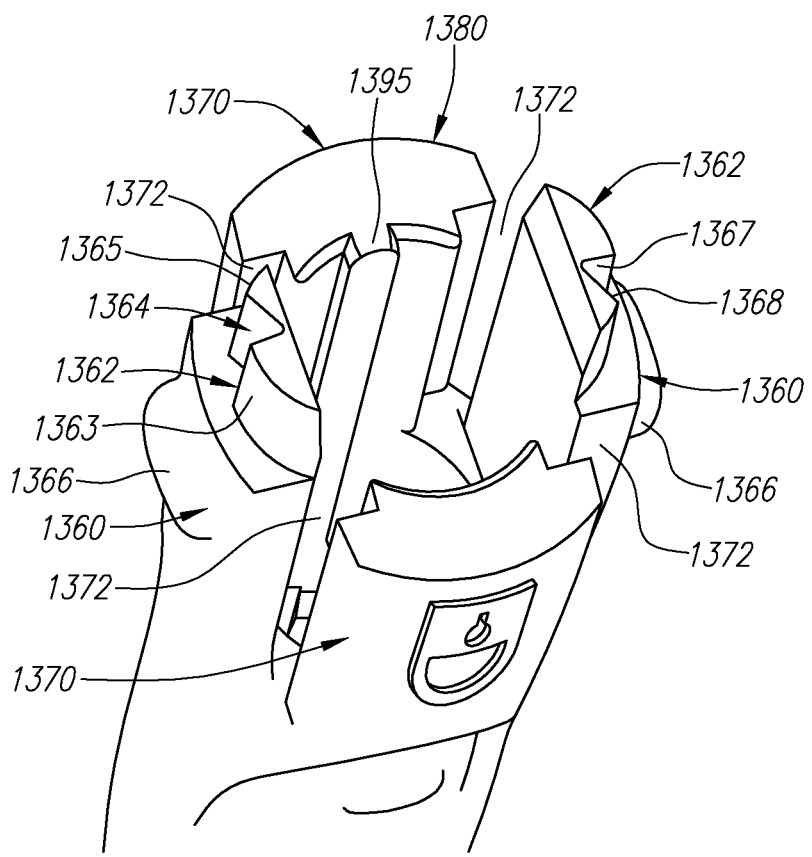
FIG. 13 is a partial schematic view of the proximal end of the hub cap shown in FIG. 7.

Referring to FIGS. 7-8, a catheter hub assembly 1010 in accordance with another embodiment includes a hub body 1100, a hub knob 1200, and a hub cap 1300. Hub body 1100 has a proximal end 1110 and a distal end 1180, with a shaft 1130 extending between the proximal end 1110 and the distal end 1180. Shaft 1130 has an exterior surface 1132 and an inner through lumen 1133. The proximal end 1110 of the hub body 1100 may include a Luer lock 1115 for connection with other apparatuses. The hub body 1100 may include a collar 1120.

The shaft 1130 of the hub body 1100 may include a recessed area 1140 for receiving an O-ring. A suture hole 1150 is disposed in the recessed area 1140 extending to the inner lumen 1133 to allow one or more suture wires to pass through. The O-ring seals the suture hole 1150 to ensure that the catheter hub 1010 does not leak.

The hub body 1100 may further include a flair element 1185 and a snap ring 1190 located adjacent the distal end 1180 of the hub body 1100, and an alignment keyway 1195 extending from adjacent the distal end 1180 of the hub body 1100 longitudinally along the outer surface 1132 of the hub body 1100 toward the proximal end 1110. The flair element 1185 of the hub body 1100 is adapted to mate with a catheter. Opposing recesses 1176 and 1177 are formed along the exterior surface 1132 of the hub body 1100 increasing in depth as they extend toward the proximal end 1110 of the hub body 1100.

Referring to FIGS. 7-11, the hub knob 1200 has a proximal end 1210, a distal end 1280, an exterior surface 1232 and an inner through lumen 1233 into which is received the shaft 1130 of hub body 1100 such that hub knob 1200 is displaceable, e.g. rotatable relative to hub body 1100. Preferably, collar 1120 fits within the proximal end 1210 of the hub knob abutting arcuate stop 1278 such that the proximal face of the collar 1120 is flush with the peripheral edge of proximal end 1210 of hub knob 1200. Hub knob 1200 may also include a suture hole 1250 extending from the exterior surface 1232 to inner lumen 1233. A groove 1275 defining a first stop portion 1276 and a second stop portion 1277 may be disposed internally adjacent the proximal end 1210 of the hub knob 1200. Limit member 1125 extending from the collar 1120 of the hub body 1100 is received in groove 1275 and engages stop portions 1276 or 1277 to limit rotation of the hub knob 1200.

Referring to FIGS. 7-13, hub cap 1300 has a proximal end 1310, a distal end 1380 and an inner through lumen 1333. Hub cap 1300 may also include a snap groove along the inner through lumen 1333 adjacent the distal end 1310 and an alignment key 1395 extending along the inner through lumen 1333. Preferably, the alignment key 1395 of hub cap 1300 is received within alignment keyway 1195 of hub body 1100 to properly align the hub body 1100 with hub cap 1300. Snap ring 1190 of the hub body 1100 fits into the snap groove (see, e.g., 390 in FIG. 4) of the hub cap 1300 to secure the hub body 1100 to the hub cap 1300. The distal end 1380 of the hub cap 1300 is adapted to capture a catheter to be secured to the flair element 1185 of the hub body 1100 when the catheter hub 1010 is assembled. The exterior surface 1332 of the hub cap 1300 may have a depression 1302 that can be used to identify the catheter French size of the device.

Preferably the proximal end 1310 of the hub cap 1300 is divided into two opposing resilient members 1360 and two opposing non-resilient members 1370 with adjacent resilient and non-resilient members 1360 and 1370 being in spaced relation with gaps 1372 extending longitudinally between members 1360 and 1370. The resilient members 1360 are outwardly spring biased. Catch or locking members 1362 preferably extend proximally from resilient members 1360.

The catch members 1362 have a first ramped or arcuate forward surface 1363, a second ramped or arcuate rear surface 1365 and a recessed catch 1364 formed there between. Catch tabs 1260 formed on the interior of the hub knob 1200 cooperate with the catch members 1362 to positively position the hub knob 1200 in the locked and unlocked positions. As the hub knob 1200 is rotated toward the locked position, the catch tabs 1260 engage the ramped surface 1363 of the catch members 1362 deflecting the resilient members 1360 inward toward the hub shaft 1130. When the catch tabs 1260 reach the recessed catches 1364, the resilient members 1360 because of their spring bias spring outward toward the hub knob 1200 giving a snap like feel to the positioning of the hub knob 1200 in the locked position. Further rotation of the hub knob 1200 is prevented by one of the stop portions 1276 or 1277 defined by the groove 1275 in the hub knob 1200 and the limit member 1125 of the hub body 1100.

To release the hub knob 1200 and rotate it from a locked position to an unlocked position, buttons 1366 formed on the exterior of the resilient members 1360 are pressed to deflect the resilient members 1360 inward and release the catch tabs 1260 from the recessed catches 1364. As the hub knob 1200 is rotated toward the unlocked position, the catch tabs 1260 engage the second ramped surface 1365 of the catch members 1362 deflecting the resilient members 1360 inward toward the hub shaft 1130. When the catch tabs 1260 reach the recessed catches 1364, the resilient members 1360 move outward toward the hub knob 1200 to positively position the hub knob 1200 in the unlocked position. Further rotation of the hub knob 1200 is prevented by one of the stop portions 1276 or 1277 defined by the groove 1275 in the hub knob 1200 and the limit member 1125 of the hub body 1100.

Preferably, the recessed catch 1364 has a first surface 1367 that acts as a stop to prevent rotation of the hub knob 1200 from the locked to the unlocked position without deflecting the resilient members 1360 inward, and a ramped surface 1368 that the catch tabs 1260 engage to deflect the resilient members 1360 inward to allow the hub knob 1200 to rotate from the unlocked position to the locked position.

Figure 14:
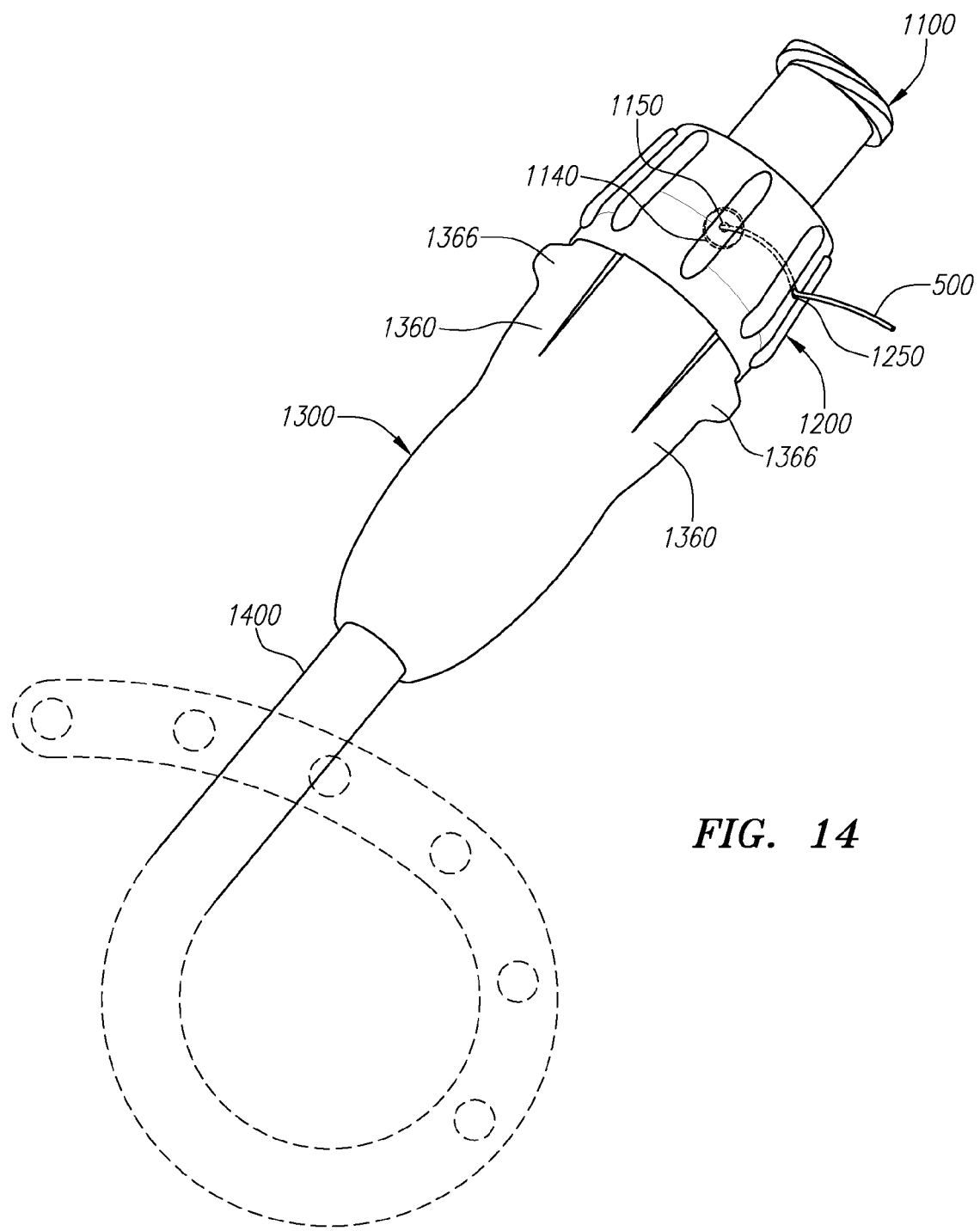
FIG. 14 is an assembled view of the catheter hub and catheter assembly shown in FIG. 7 in a locked position.

Referring to FIG. 14, the catheter hub assembly 1010 is shown with the hub knob 1200 being disposed in a locked position in which the suture holes 1250 and 1150 offset from one another. As a result, the suture wire 500 is locked in place between the hub knob 1200 and the hub body 1100 extending between suture holes 1250 and 1150 which effects holding the flexible end of catheter 1400 into a pigtail configuration.

It will be apparent to those skilled in the art that various modifications and variations can be made in the apparatus and method of the present invention without departing from the spirit or scope of the invention. Thus, it is intended that the present invention cover the modifications and variations of this invention provided they come within the scope of the appended claims and their equivalents.

We claim:
1. A catheter hub assembly comprising:
a hub knob member having an outer surface, an inner surface, and a through lumen, a suture hole extending from the outer surface to the inner surface through the lumen of the hub knob member, and the inner surface of the hub knob member having a first catch tab and a second catch tab;
a hub body member co-axially aligned within the inner surface of the hub knob member, the hub body member further comprising an exterior surface, an inner through lumen, a suture hole extending from the exterior surface of the hub body member to the inner lumen of the hub body member and a locking element disposed on the exterior surface of the hub body member;

a hub cap member, the hub cap member further comprising an exterior surface, a first resilient member and a second resilient member, a first non-resilient member and a second non-resilient member, the first resilient member having a first catch member and the second resilient member having a second catch member; and the first catch tab aligns with the first catch member and the second catch tab aligns with the second catch member.

2. A catheter hub assembly as recited in claim 1, wherein the locking element of the hub body having a raised portion extending from the exterior surface of the hub body, and having a stop portion and wherein the locking member of the hub knob disposed adjacent to the locking element of the hub body and having a stop surface such that when the hub knob member is rotated to the second position, the stop surface engages the stop portion of the locking element to inhibit rotation of the hub knob member towards the first position.

3. A catheter hub assembly as recited in claim 2, wherein the locking element of the hub body comprises a ramp surface extending from the exterior surface of the hub body to the stop portion of the locking element of the hub body.

4. A catheter hub assembly as recited in claim 1, wherein the suture hole of the hub body is disposed in a recess portion in the exterior surface of the hub body and wherein a resilient sealing member is disposed in said recess portion and has normally sealed hole aligned with the suture hole of the hub knob, the normally sealed hole being configured to receive and seal against a tension member.

5. A catheter hub assembly as recited in claim 1 that comprises a tension member disposed through the suture holes of the hub body and hub knob member and extending out of the exterior surface of the hub knob, the tension member being freely movable when the hub knob is in the first position and inhibited from movement when the hub knob is in the second position.

6. A catheter hub assembly as recited in claim 1, wherein the locking element of the hub cap comprises a ramp surface.

7. A catheter hub assembly comprising:

a hub knob member having an inner surface and a through lumen, a suture hole, and the inner surface of the hub knob member having a first catch tab and a second catch tab;

a huh body member having an exterior surface, an inner through lumen, a suture hole extending from the exterior surface of the hub body member to the inner lumen of the hub body member; and a hub cap member, a first resilient member and a second resilient member, a first non-resilient member and a second non-resilient member, the first resilient member having a first catch member and the second resilient member having a second catch member.

8. A catheter hub assembly as recited in claim 7, further comprising the hub body having a locking element disposed on an outer surface of the hub body.

9. A catheter hub assembly as recited in claim 8, wherein the locking element includes a ramp.

10. A catheter hub assembly as recited in claim 7, wherein the hub body member is co-axially aligned within the inner surface of the hub knob member.

11. A catheter hub assembly as recited in claim 7, further comprising the first catch tab aligns with the first catch member and the second catch tab aligns with the second catch member.

* * * * *